(12) United States Patent
Homolya et al.

(10) Patent No.: US 7,122,329 B2
(45) Date of Patent: Oct. 17, 2006

(54) SIMPLE QUANTITATIVE FLUORESCENT ASSAY METHOD FOR DETERMINING THE ACTIVITY OF TRANSPORT PROTEINS OF INTEREST

(75) Inventors: László Homolya, Budapest (HU); Balázs Sarkadi, Ágnes st. (HU); Raymond Evers, East Brunswick, NJ (US)

(73) Assignee: Solvo Biotechnology, Szeged (HU)

( * ) Notice: Subject to any disclaimer, the term of this patent is extended or adjusted under 35 U.S.C. 154(b) by 322 days.

(21) Appl. No.: 10/312,857

(22) PCT Filed: Jul. 3, 2001

(86) PCT No.: PCT/HU01/00074

§ 371 (c)(1),
(2), (4) Date: Jul. 24, 2003

(87) PCT Pub. No.: WO02/03066

PCT Pub. Date: Jan. 10, 2002

(65) Prior Publication Data

US 2004/0033508 A1    Feb. 19, 2004

(30) Foreign Application Priority Data

Jul. 3, 2000    (HU) .................... 0002557

(51) Int. Cl.
*G01N 33/567*    (2006.01)
(52) U.S. Cl. .................... 435/7.21
(58) Field of Classification Search .............. None
See application file for complete search history.

(56) References Cited

OTHER PUBLICATIONS

R. Evers et al. (1998) "Drug export activity of the human canalicular multispecific organic anion transporter in polarized kidney MDCK cells expressing cMOAT (MRP2) cDNA," Journal of Clinical Investigation vol. 101, pp. 1310-1319.*

L. Homolya et al. (1996) "A new method for quantitative assessment of P-glycoprotein-related multidrug resistance in tumour cells," British Journal of Cancer vol. 73, pp. 849-855.*

N. Feller et al. (1995) "ATP-dependent efflux of calcein by the multidrug resistance protein (MRP): no inhibition by intracellular glutathione depletion," FEBS Letters vol. 368, pp. 385-388.*

* cited by examiner

*Primary Examiner*—Sandra E. Saucier
(74) *Attorney, Agent, or Firm*—Hahn & Voight PLLC

(57) ABSTRACT

The invention relates to a simple quantitative fluorescent assay method for determining the activity of transport proteins, more specifically multi-drug resistance associated proteins (MRPs). The method of the invention is performed on a well sealed culture of polarized cells expressing a transport protein of interest grown to confluency on a permeable support, said confluent cell culture forming well separated apical and basolateral compartments. The cells are contacted with a cell permeable non-fluorescent derivative of a fluorescent compound (e.g. calcein AM) in one compartment and, after a certain period of incubation, the fluorescence intensity detected in a sample taken from the opposite compartment is indicative of the activity of the transport protein of interest expressed in the cells. The invention also concerns methods for the qualitative and quantitative determination of inhibitors and activators of transport proteins of interest and methods for assessing basolateral and/or apical localization of plasma membrane bound transport proteins of interest in polarized cells.

19 Claims, 3 Drawing Sheets

SIMPLE QUANTITATIVE FLUORESCENT ASSAY METHOD FOR DETERMINING THE ACTIVITY OF TRANSPORT PROTEINS OF INTEREST

The invention relates to a simple quantitative fluorescent assay method for determining the activity of transport proteins of interest, more specifically multi-drug resistance associated proteins (MRPs).

The method of the invention is performed on a well sealed culture of polarized cells expressing a transport protein of interest grown to confluency on a permeable support, said confluent cell culture forming well separated apical and basolateral compartments. The cells are contacted with a cell permeable non-fluorescent derivative of a fluorescent compound (e.g. calcein AM) in one compartment and, after a certain period of incubation, the fluorescence intensity detected in a sample taken from the opposite compartment is indicative of the activity of the transport protein of interest expressed in the cells.

The invention also concerns methods for the qualitative and quantitative determination of inhibitors and activators of transport proteins of interest and methods for assessing basolateral and/or apical localization of plasma membrane bound transport proteins of interest in polarized cells.

BACKGROUND OF THE INVENTION

The multi-drug resistance proteins (MDRs) and the multi-drug resistance associated proteins, MRP1 and MRP2 are members of the ABC-transporter superfamily, and may cause multiple drug resistance in malignant tumors. By now, at least six MRP-like proteins have been identified. The physiological role of these proteins may range from elimination of toxic agents to diverse secretory function, predominantly in epithelial cells. MRP1 is widely expressed in various tissues, while MRP2 is predominantly expressed in hepatocytes and epithelial cells of renal proximal tubules. Identifying novel compounds effectively inhibiting such transport proteins is, therefore, a major interest in trying to elaborate more effective chemotherapeutical treatment methods for drug resistant type of malignant disorders. Identifying activators of said transport proteins might also be of interest in other applications where the enhancement of their activity may help in the elimination of some undesired physiological states.

It has been previously shown that MRP1 extrudes negatively charged fluorescent compounds, e.g. calcein free acid, from the cells [Feller et al, FEBS Lett. 368, 385–388 (1995); Holló et al, FEBS Lett. 383, 99–104 (1996)]. We have recently found that this dye is rapidly expelled from cells also by MRP2. It is also possible that other members of this protein family transport this compound. In polarized cells, the distribution of these proteins is not homogeneous. Expression of MRP1 is restricted to the basolateral surface, while MRP2 is expressed solely in the apical membrane.

This feature makes possible the assessment of the function of these and other similar proteins in the so called vectorial transport assay performed on confluent cultures of polarized cells grown on permeable solid support (e.g. on porous membranes). The vectorial transport assay described so far [Evers, R. et al, J. Clin. Invest. 97, 1211–1218 (1996)], though being suitable to experimentally investigate the localization and activity of transport proteins like MRP1 and MRP2, suffers from the serious drawback of using exclusively radioactively labeled substrates for detection which, of course, requires the application of extra laboratory safety equipment and regulations. Another drawback is the previously described vectorial transport assay is that certain labeled substrates used for the assessment of the activity of the intracellular transport proteins of interest might be able to pass the tight junctions contacting the cells of the confluent culture used and, therefore, can get to the opposite compartment even without being transported, thus making very complicated to develop a suitable quantitative assay for the exact determination of the activity of the transport proteins of interest.

It is, therefore, an object of the present invention is to provide simple qualitative and quantitative vectorial transport assay methods that are significantly easier to perform and automate than the previously described ones and can also be made quantitative by only detecting the transcellular export (and not the transport going possibly through the tight junctions of the polarized culture and thereby avoiding uptake and excretion by the cells). Another object of the present invention is to provide assay methods for the identification of inhibitors and activators of transport proteins of interest and, also, assay methods for the fast and easy assessment of the localization of transport proteins of interest in the basolateral and/or apical plasma membrane.

Calcein is a well known fluorescent substance (commercialized by Molecular Probes, Inc. USA) and the non-fluorescent acetoxy-methyl ester derivative of said compound (calcein AM) is known to be cell permeable due to its hydrophobic character. We have previously developed different assay arrangements using calcein AM for the assessment of the activity of MDR1 or other transport proteins which can extrude calcein AM from the cells but can not extrude calcein itself (U.S. Pat. No. 5,872,014; European Patent No. 0,784,699). We now have recognized that calcein and calcein AM (and other compounds of similar behavior) can also be used to elaborate assay methods for the assessment of the activity of MRP1, MRP2 and similar transport proteins which can effectively extrude calcein out from the cells.

DETAILED DESCRIPTION OF THE INVENTION

The method of the invention is performed on a well sealed culture of polarized cells expressing a transport protein of interest grown to confluency (with tight junctions having been formed) on permeable supports (e.g. on porous membranes or collagen matrixes) and forming thereby well separated apical and basolateral compartments. The cell culture is contacted with a cell permeable non-fluorescent derivative of a fluorescent compound (e.g. calcein AM) in one compartment, which derivative is then taken up by and cleaved within the cells to produce a fluorescent compound (e.g. calcein), which fluorescent compound is a substrate of the membrane bound transport protein of interest. The fluorescence intensity detected in a sample taken from the opposite compartment is then indicative of the actual activity of the membrane bound transport protein of interest excreting said fluorescent compound from the cells (see FIG. 1). Control experiments can be performed with similar cultures not expressing MRPs. The invention also concerns methods for the qualitative and quantitative determination of the localization, inhibitors and/or activators of transport proteins of interest. To determine the interaction between certain compounds and transport proteins of interest, the method of the invention is performed in the presence of the compound to be examined. The studied compound can be added to either the apical or the basolateral or both sides of the cell culture depending on the question to be answered.

The present invention therefore provides a method for determining the activity and/or quantity of a transport protein of interest being localized either to the basolateral or to the apical plasma membrane of polarized cells comprising the steps of:
(a) providing a well sealed confluent culture of polarized cells supposed to express said transport protein of interest grown on a permeable support, ensuring the formation of tight junctions among said cells of said culture, forming thereby separate basolateral and apical compartments on the opposite sides of said confluent cell culture;
(b) adding a cell permeable non-fluorescent derivative of a fluorescent compound into one of the compartments, which is opposite to the plasma membrane of said polarized cells where the transport protein of interest is localized, said derivative being cleavable by intracellular enzymes to form a fluorescent compound that is a substrate of said transport protein of interest;
(c) incubating the cells in the presence of said non-fluorescent derivative;
(d) measuring the fluorescence intensity of a sample taken from the compartment opposite to the one where said non-fluorescent derivative was added, said intensity being indicative of the presence and activity of said transport protein of interest; and optionally
(e) calculating the measure of activity and/or quantity of said transport protein of interest being present in said cells on the basis of the fluorescence intensity value measured in step (d) and on calibration curves and/or empirical correlations established previously.

The invention also provides a method for determining the ability of a test compound of interest to inhibit or enhance the activity of a transport protein of interest being localized either to the basolateral or to the apical plasma membrane of polarized cells comprising the steps of:
(a) providing a well sealed confluent culture of polarized cells expressing said transport protein of interest grown on a permeable support, ensuring the formation of tight junctions among said cells of said culture, forming thereby separate basolateral and apical compartments on the opposite sides of said confluent cell culture;
(b) adding a cell permeable non-fluorescent derivative of a fluorescent compound into one of the compartments, which is opposite to the plasma membrane of said polarized cells where the transport protein of interest is localized, said derivative being cleavable by intracellular enzymes to form a fluorescent compound that is a substrate of said transport protein of interest;
(c) incubating the cells in the presence of said non-fluorescent derivative;
(d) measuring the fluorescence intensity of a sample taken from the compartment opposite to the one where said non-fluorescent derivative was added, said intensity being indicative of the presence and activity of said transport protein of interest; and optionally
(e) calculating the measure of activity of said transport protein of interest being present in said cells on the basis of the fluorescence intensity value measured in step (d) and calibration curves and/or empirical correlations established previously;
(a) repeating the same steps (b)–(ed) using the same polarized cell culture provided in step (a) or a polarized cell culture essentially identical to that while ensuring that said test compound of interest or any metabolite of interest produced from said test compound of interest within said cells be contacted with said transport protein of interest in repeatedly executed step (c); and
(b) comparing the fluorescence intensity values measured in step (d) and in repeatedly executed step (d) and/or comparing the activity values calculated in step (ed) and in repeatedly executed step (ed) and determining whether the test compound of interest inhibits or enhances the activity of said transport protein of interest.

The invention further concerns a method for assessing basolateral and/or apical localization of a plasma membrane bound transport protein of interest in polarized cells comprising the steps of:
(a) providing a well sealed confluent culture of polarized cells expressing said transport protein of interest grown on a permeable support, ensuring the formation of tight junctions among said cells of said culture, forming thereby separate basolateral and apical compartments on the opposite sides of said confluent cell culture;
(b) adding a cell permeable non-fluorescent derivative of a fluorescent compound into both the apical and basolateral compartments, said derivative being cleavable by intracellular enzymes to form a fluorescent compound that is a substrate of said transport protein of interest;
(c) incubating the cells in the presence of said non-fluorescent derivative;
(d) measuring the fluorescence intensity of a sample taken from both compartments;
(e) comparing the fluorescence intensity values measured in the different compartment, said comparison being indicative of apical and/or basolateral localization of said transport protein of interest; and optionally
(f) calculating the percentage apical and/or basolateral localization of said transport protein of interest being present in said cells on the basis of the fluorescence intensity values measured in step (d) and calibration curves and/or empirical correlations established previously.

Said fluorescent compound used in the method of the invention is advantageously calcein and said non-fluorescent derivative of said fluorescent compound is a cell permeable non-fluorescent derivative of calcein, advantageously calcein AM.

The method of the invention is advantageously performed on polarized kidney cells, more advantageously MDCK II cells, with said incubation occuring at about 37° C. for about 30 minutes.

Several advantageous embodiments of the invention will be further illustrated by the below-presented experimental examples which are not intended to be limiting as to the scope of the invention which, in turn, is defined by the appended claims.

EXAMPLE 1

Inhibitory Effect of MRP2 Substrates on Vectorial Calcein Transport

Figure 1:
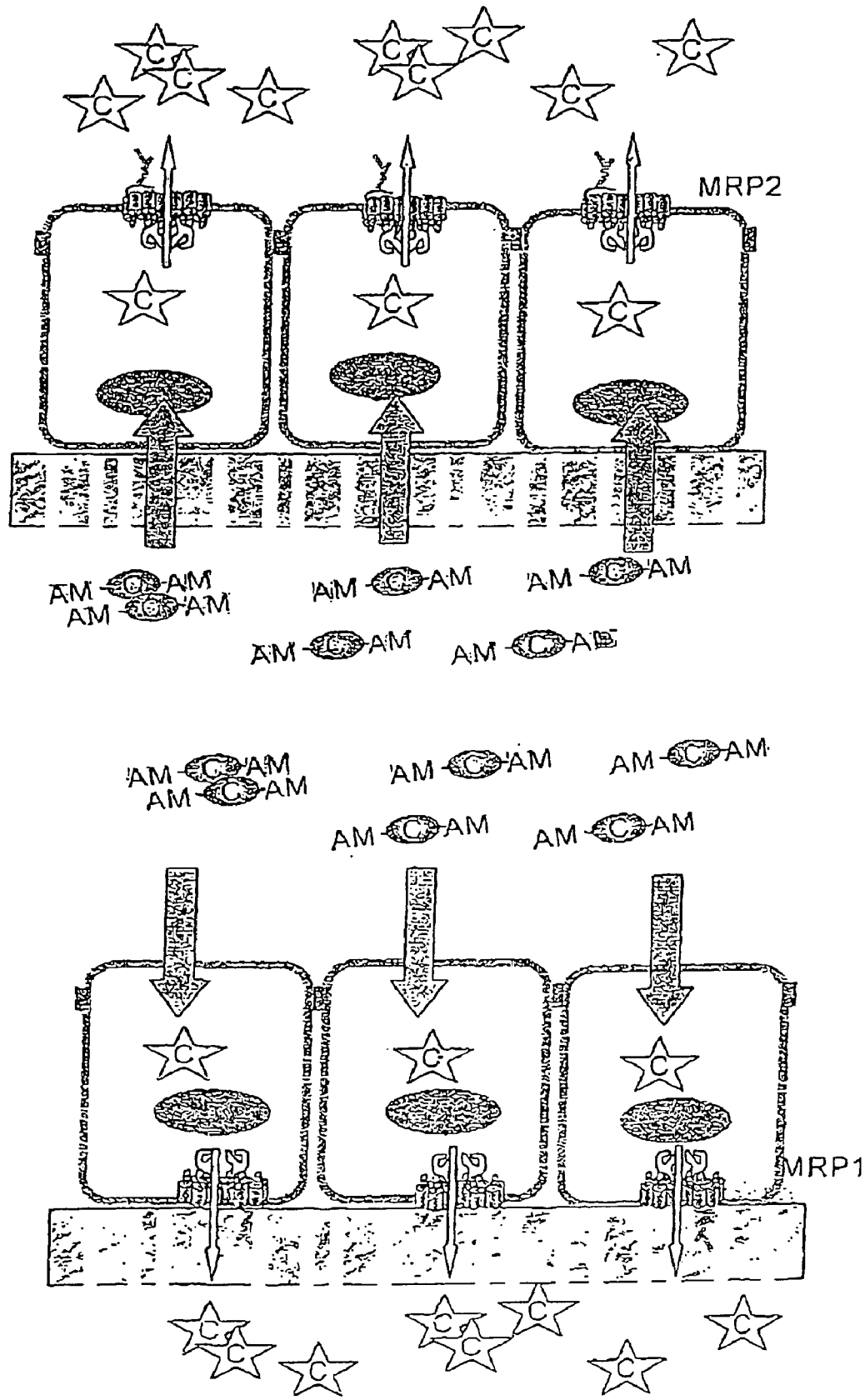
FIG. 1 is the scheme of the transport measurement assay of the invention (abbreviations: C: fluorescent compound; C-AM: Non fluorescent derivative of C).
Figure 2:
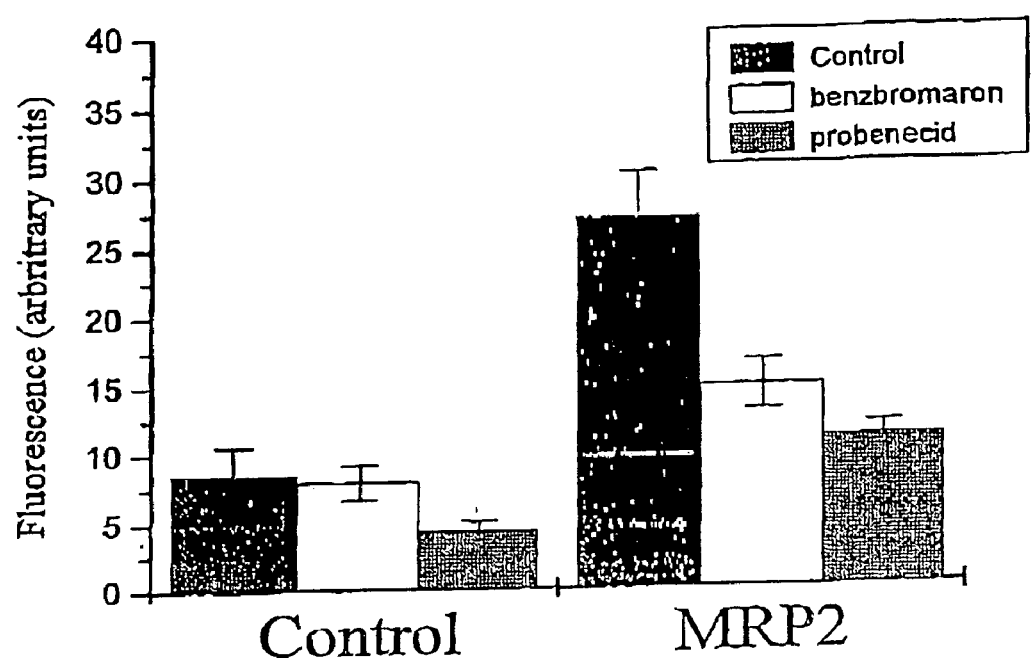
FIG. 2 shows the inhibitory effect of two MRP2 substrates on the vectorial transcellular calcein transport as determined by the assay of the invention.

Polarized canine kidney cells (MDCK II) and its derived cell line stably expressing the human MRP 2 were seeded onto Traswell-Col membrane supports (4 μm in pore size), and the cultures were maintained for 7 days in D-MEM medium containing 10% FBS and antibiotics. After washing the cultures, 200 μl and 400 μl Ringer's buffer was added to the upper and lower compartments, respectively. The cells were bilaterally pre-incubated for 5 minutes with the examined drugs as indicated. The cells were then exposed to 5 μM calcein-AM on the basolateral side (lower chamber) for 30 minutes at 37° C. A 100 μl sample was taken from the apical compartment (upper chamber) and its fluorescence was determined. In FIG. 2, the left columns show the results with parental cells, while right columns indicate what was obtained with cells expressing MRP2. Solid bars depicts the fluorescence in arbitrary units measured in the absence of any drug, open and gray bars indicate the results obtained in the presence of 25 μM benzbromaron and 1 μM probenecid, respectively.

EXAMPLE 2

Export of Calcein by MDCK II Cell Monolayers

Figure 3:
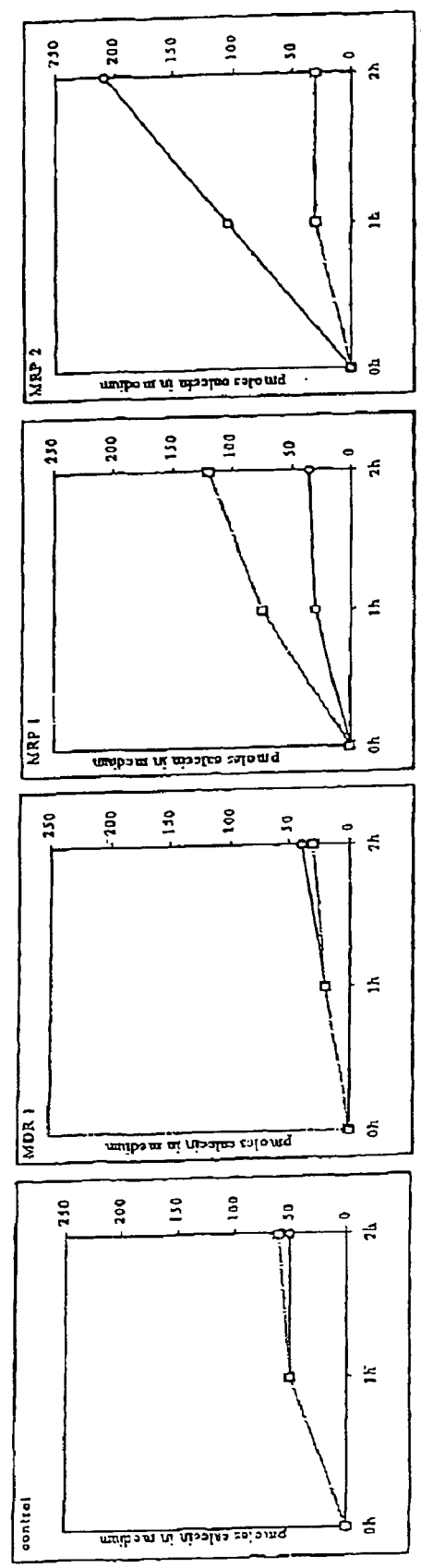
FIG. 3 shows the export of calcein by MDCK II cell monolayers. Calcein AM was added to both the apical and basolateral medium, and the amount of calcein appearing in the medium was measured. Samples were taken at 1 and 2 h Squares: export to apical compartment. Circles: export to basolateral compartment.

Polarized cells were seeded on microporous polycarbonate filters (3 μm pore size, 24.5 mm diameter) and cultured for 3 days with a daily medium replacement. The experiment was started by replacing the medium at either the apical or the basal side of the cell layer. Export of calcein was determined by incubating monolayers in HBSS containing calcein AM (1 μM) at room temperature. Samples (200 ml) from each compartment were taken at the time-points indicated. 800 ml HBSS was added and fluorescence was determined. The amount of calcein exported was calculated using a calibration curve made with free calcein. Results are shown in FIG. 3.

As demonstrated above via advantageous embodiments of the invention, the methods of the invention are suitable for the simple qualitative and quantitative assessment of the activity of MRP like transport proteins of interest, for the identification of inhibitors and activators of said transport proteins and for the fast and easy assessment of the localization of such proteins in the basolateral and/or apical plasma membrane. Persons skilled in the art will certainly understand that numerous variations and modification of the described methods of the invention can be elaborated by applying alternative solutions equivalent to those described herein, such variations and modifications, however, will not diverge from the original spirit of the invention and, therefore, remain within the scope of the invention as defined by the appended claims.

The invention claimed is:

1. A method for determining the activity and/or quantity of a transport protein of interest being localized either to the basolateral or to the apical plasma membrane of polarized cells comprising the steps of:
   (a) providing a well sealed confluent culture of polarized cells supposed to express said transport protein of interest grown on a permeable support, ensuring the formation of tight junctions among said cells of said culture, forming thereby separate basolateral and apical compartments on the opposite sides of said confluent cell culture;
   (b) adding a cell permeable non-fluorescent derivative of a fluorescent compound into one of the compartments, which is opposite to the plasma membrane of said polarized cells where the transport protein of interest is localized, said derivative being cleavable by intracellular enzymes to form a fluorescent compound that is a substrate of said transport protein of interest;
   (c) incubating the cells in the presence of said non-fluorescent derivative;
   (d) measuring the fluorescence intensity of a sample taken from the compartment opposite to the one where said non-fluorescent derivative was added, said intensity being indicative of the presence and activity of said transport protein of interest; and optionally
   (e) calculating the measure of activity and/or quantity of said transport protein of interest being present in said cells on the basis of the fluorescence intensity value measured in step (d) and on calibration curves and/or empirical correlations established previously.

2. The method according to claim 1 wherein said fluorescent compound is calcein and said non-fluorescent derivative of said fluorescent compound is calcein AM.

3. The method according to claim 1 wherein said polarized cells are kidney cells.

4. The method according to claim 1 wherein the incubation in step (c) takes place at about 37° C. for about 30 minutes.

5. The method according to claim 1 wherein the transport protein of interest is MRP 1 or MRP2.

6. A method for determining the ability of a test compound of interest to inhibit or enhance the activity of a transport protein of interest being localized either to the basolateral or to the apical plasma membrane of polarized cells comprising the steps of:
   (a) providing a well sealed confluent culture of polarized cells expressing said transport protein of interest grown on a permeable support, ensuring the formation of tight junctions among said cells of said culture, forming thereby separate basolateral and apical compartments on the opposite sides of said confluent cell culture;
   (b) adding a cell permeable non-fluorescent derivative of a fluorescent compound into one of the compartments, which is opposite to the plasma membrane of said polarized cells where the transport protein of interest is localized, said derivative being cleavable by intracellular enzymes to form a fluorescent compound that is a substrate of said transport protein of interest;
   (c) incubating the cells in the presence of said non-fluorescent derivative;
   (d) measuring the fluorescence intensity of a sample taken from the compartment opposite to the one where said non-fluorescent derivative was added, said intensity being indicative of the presence and activity of said transport protein of interest; and, optionally, calculating the measure of activity of said transport protein of interest being present in said cells on the basis of the fluorescence intensity value measured and calibration curves and/or empirical correlations established previously;
   (e) repeating steps (b)–(d) using the same polarized cell culture provided in step (a) or a polarized cell culture essentially identical to that while ensuring that said test compound of interest or any metabolite of interest produced from said test compound of interest within said cells be contacted with said transport protein of interest in repeatedly executed step (c); and (f) comparing the fluorescence intensity values measured in step (d) and in repeatedly executed step (d) and/or comparing the activity values calculated in step (d) and in repeatedly executed step (d) and determining whether the test compound of interest inhibits or enhances the activity of said transport protein of interest.

7. The method according to claim 6 wherein said fluorescent compound is calcein and said non-fluorescent derivative of said fluorescent compound is a cell permeable non-fluorescent derivative of calcein.

8. The method according to claim 6 wherein said polarized cells are kidney cells.

9. The method according to claim 6 wherein the incubation in step (c) takes place at about 37° C. for about 30 minutes.

10. The method according to claim 6 wherein the transport protein of interest is a member of the ABC-transporter superfamily.

11. The method according to claim 10 wherein the transport protein of interest is a multi-drug transporter or multi-drug transporter related protein.

12. The method according to claim 11 wherein the transport protein of interest is MRP1 or MRP2.

13. The method according to claim 6 wherein said fluorescent compound is calcein and said non-fluorescent derivative of said fluorescent compound is calcein AM.

14. The method according to claim 6 wherein said polarized cells are MDCK II cells.

15. A method for assessing basolateral and/or apical localization of a plasma membrane bound transport protein of interest in polarized cells comprising the steps of:

(a) providing a well sealed confluent culture of polarized cells expressing said transport protein of interest grown on a permeable support, ensuring the formation of tight junctions among said cells of said culture, forming thereby separate basolateral and apical compartments on the opposite sides of said confluent cell culture;

(b) adding a cell permeable non-fluorescent derivative of a fluorescent compound into both the apical and basolateral compartments, said derivative being cleavable by intracellular enzymes to form a fluorescent compound that is a substrate of said transport protein of interest;

(c) incubating the cells in the presence of said non-fluorescent derivative;

(d) measuring the fluorescence intensity of a sample taken from both compartments;

(e) comparing the fluorescence intensity values measured in the different compartments, said comparison being indicative of apical and/or basolateral localization of said transport protein of interest; and optionally (f) calculating the percentage apical and/or basolateral localization of said transport protein of interest being present in said cells on the basis of the fluorescence intensity values measured in step (d) and calibration curves and/or empirical correlations established previously.

16. The method according to claim 15 wherein said fluorescent compound is calcein and said non-fluorescent derivative of said fluorescent compound is calcein AM.

17. The method according to claim 15 wherein said polarized cells are kidney cells.

18. The method according to claim 15 wherein the incubation in step (c) takes place at about 37° C. for about 30 minutes.

19. The method according to claim 15 wherein the transport protein of interest is MRP 1 or MRP2.

* * * * *